United States Patent
Yang et al.

(10) Patent No.: US 11,339,197 B2
(45) Date of Patent: May 24, 2022

(54) MODIFIED EGF PROTEIN, PRODUCTION METHOD THEREFOR, AND USE THEREOF

(71) Applicant: PROGEN CO., LTD., Seoul (KR)

(72) Inventors: Zungyoon Yang, Incheon (KR); Eun Joo Nam, Seoul (KR)

(73) Assignee: PROGEN CO., LTD., Seoul (KR)

( * ) Notice: Subject to any disclaimer, the term of this patent is extended or adjusted under 35 U.S.C. 154(b) by 88 days.

(21) Appl. No.: 16/757,823

(22) PCT Filed: Oct. 23, 2018

(86) PCT No.: PCT/KR2018/012569
§ 371 (c)(1),
(2) Date: Apr. 21, 2020

(87) PCT Pub. No.: WO2019/083256
PCT Pub. Date: May 2, 2019

(65) Prior Publication Data
US 2021/0188931 A1    Jun. 24, 2021

(30) Foreign Application Priority Data

Oct. 23, 2017 (KR) .................. 10-2017-0137132
Oct. 23, 2017 (KR) .................. 10-2017-0137140
Oct. 19, 2018 (KR) .................. 10-2018-0125012

(51) Int. Cl.
| | | |
|---|---|---|
| C07K 14/485 | (2006.01) | |
| A61K 8/64 | (2006.01) | |
| A61Q 19/00 | (2006.01) | |
| C12P 21/02 | (2006.01) | |
| A61K 38/00 | (2006.01) | |

(52) U.S. Cl.
CPC ............ *C07K 14/485* (2013.01); *A61K 8/64* (2013.01); *A61Q 19/00* (2013.01); *C12P 21/02* (2013.01); *A61K 38/00* (2013.01)

(58) Field of Classification Search
CPC .......... A61K 38/00; A61K 8/64; A61Q 19/00; A61Q 19/08; C07K 14/485; C07K 2319/30; C12P 21/02
See application file for complete search history.

(56) References Cited

U.S. PATENT DOCUMENTS

| | | | |
|---|---|---|---|
| 7,517,528 B2 | 4/2009 | Wong et al. | |
| 2003/0211579 A1 | 11/2003 | Van Ness et al. | |
| 2003/0228612 A1 | 12/2003 | Kenward et al. | |
| 2006/0222653 A1* | 10/2006 | Abel ............... | A61K 47/6813 424/178.1 |
| 2015/0031611 A1 | 1/2015 | Shin et al. | |
| 2015/0133379 A1 | 5/2015 | Lee et al. | |

FOREIGN PATENT DOCUMENTS

| | | |
|---|---|---|
| KR | 10-2007-0085220 A | 8/2007 |
| KR | 10-2016-0113880 A | 10/2016 |
| WO | 03/075949 A1 | 9/2003 |
| WO | 2006/026445 A1 | 3/2006 |
| WO | 2006/049440 A1 | 5/2006 |
| WO | 2014/097733 A1 | 6/2014 |

OTHER PUBLICATIONS

Jazayeri et al., "Fc-Based Cytokines: Prospects for Engineering Superior Therapeutics", BIODRUGS, 2008, vol. 22, No. 1, p. 11-26.
Young Seok Kim, "The effect of epidermal growth factor on the scar in full thickness defect wound healing of mouse", Department of Medicine, The Graduate School, Yonsei University, 2006, pp. 28-29.
Communication from Korean Intellectual Property Office, issued in Korean Patent Application 10-2018-0125012 dated Mar. 9, 2020.
International Search Report for PCT/KR2018/012569 dated Apr. 10, 2019 [PCT/ISA/210].

* cited by examiner

*Primary Examiner* — Marcela M Cordero Garcia
(74) *Attorney, Agent, or Firm* — Sughrue Mion, PLLC

(57) ABSTRACT

A modified EGF protein, a production method therefor, and a use thereof are disclosed. The modified EGF protein allows an effective delivery of EGF into the cell and exhibits an enhanced half-life span. A method for producing the modified EGF protein includes culturing conditions where host cell growth phase and protein expression phase employ different temperature conditions. A use of the modified EGF protein is also disclosed.

25 Claims, 18 Drawing Sheets
Specification includes a Sequence Listing.

[Fig. 4A]
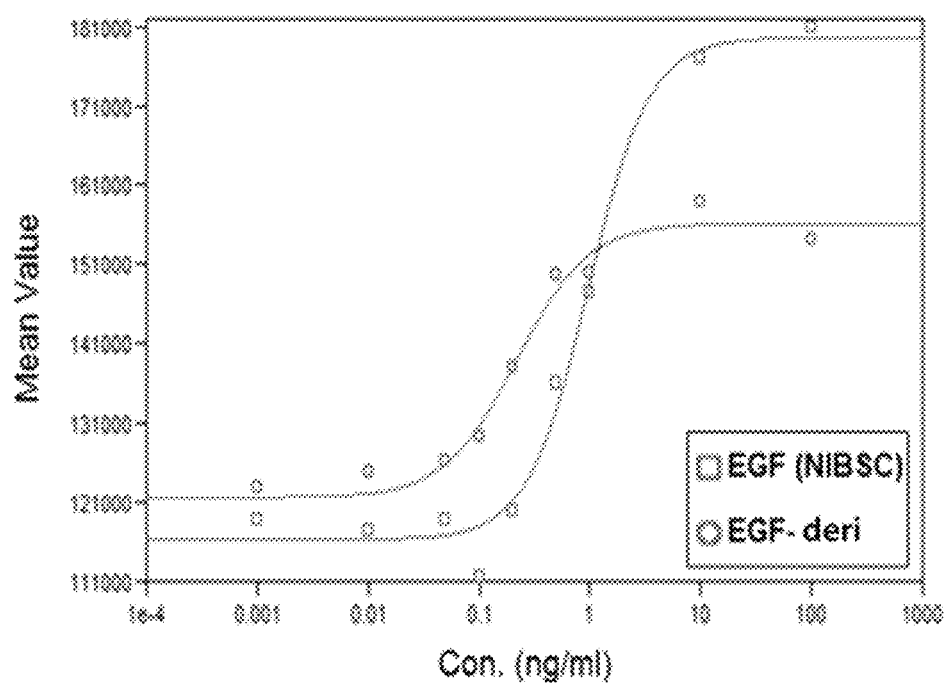

[Fig. 4B]
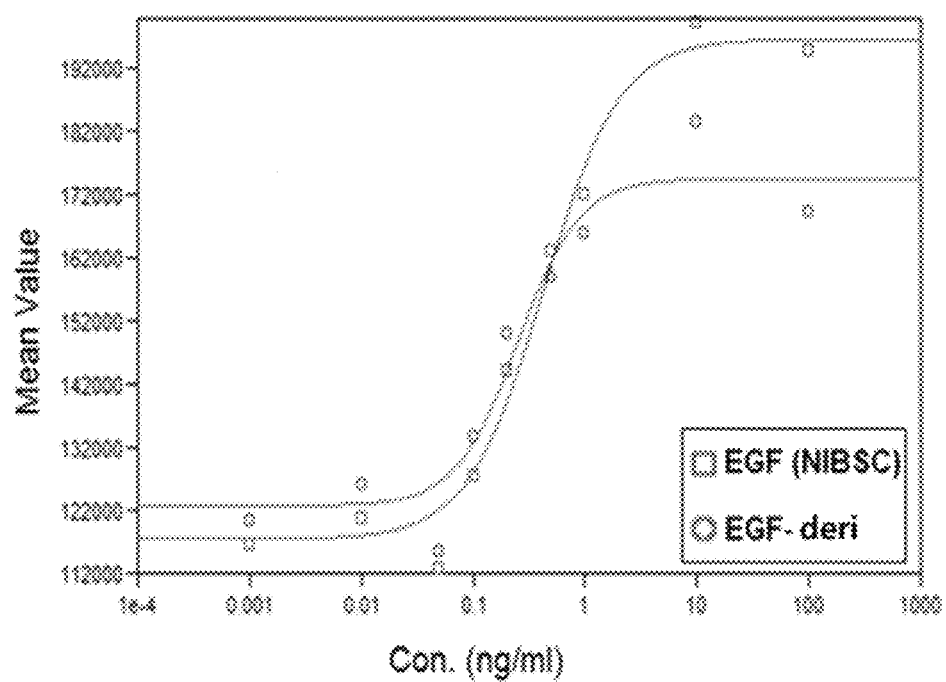

[Fig. 4C]
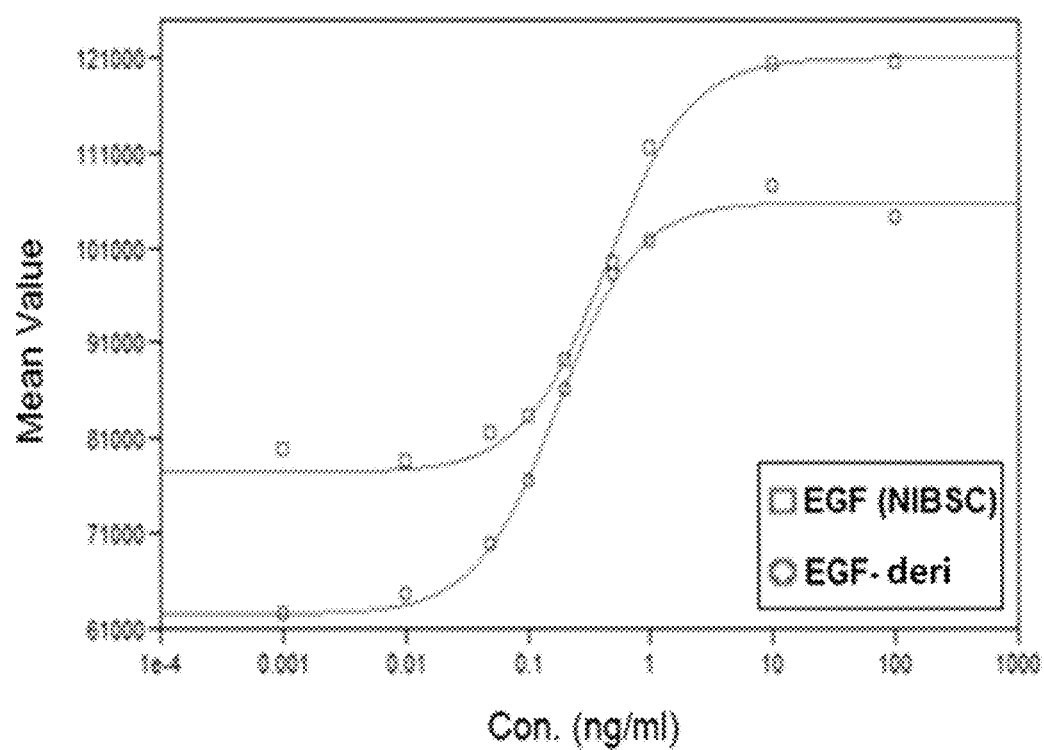

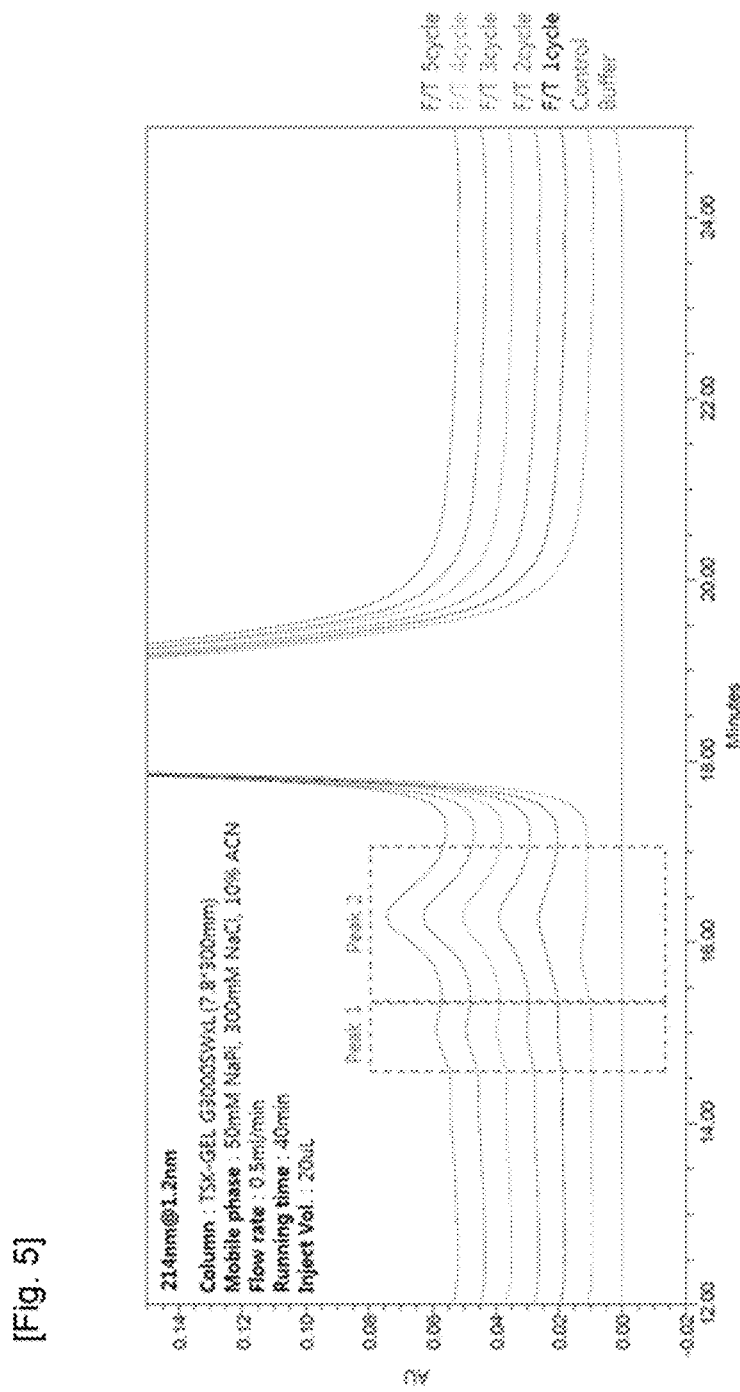
[Fig. 5]

[Fig. 6]
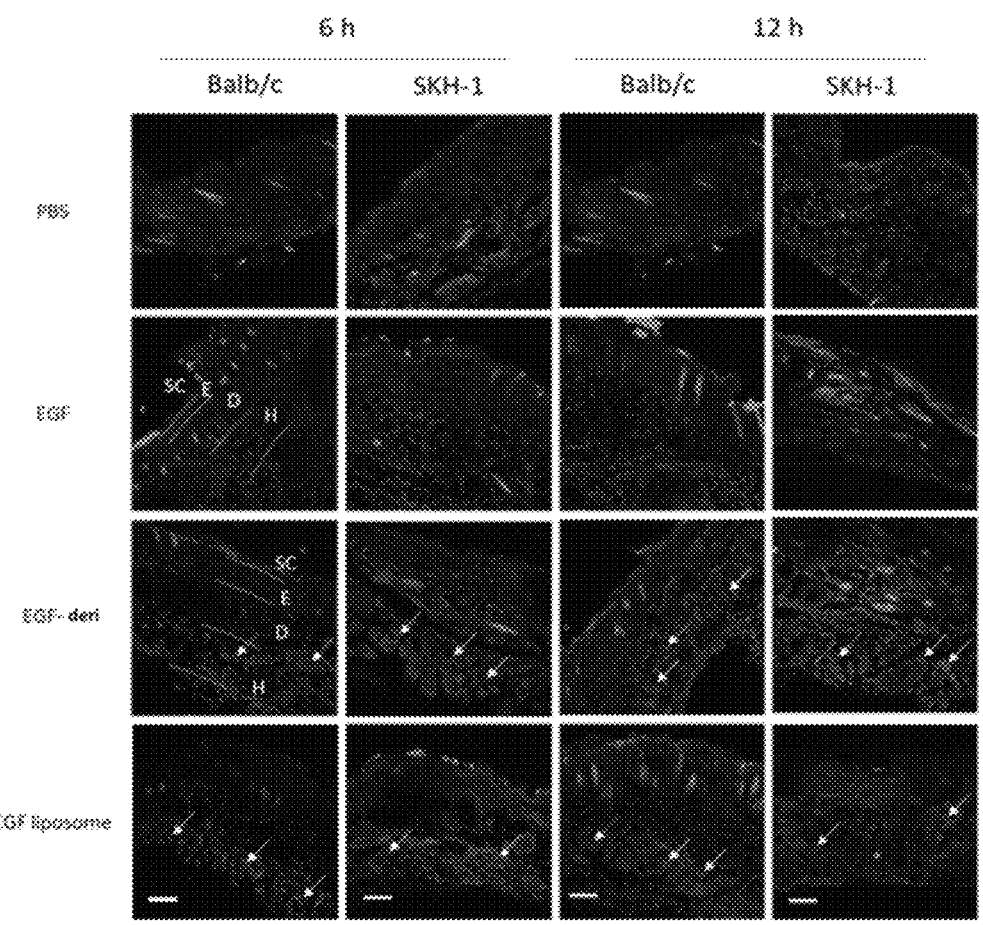
(SC: stratum corneum, E: epidermis, D: dermis, H: hypodermis)

[Fig. 7]
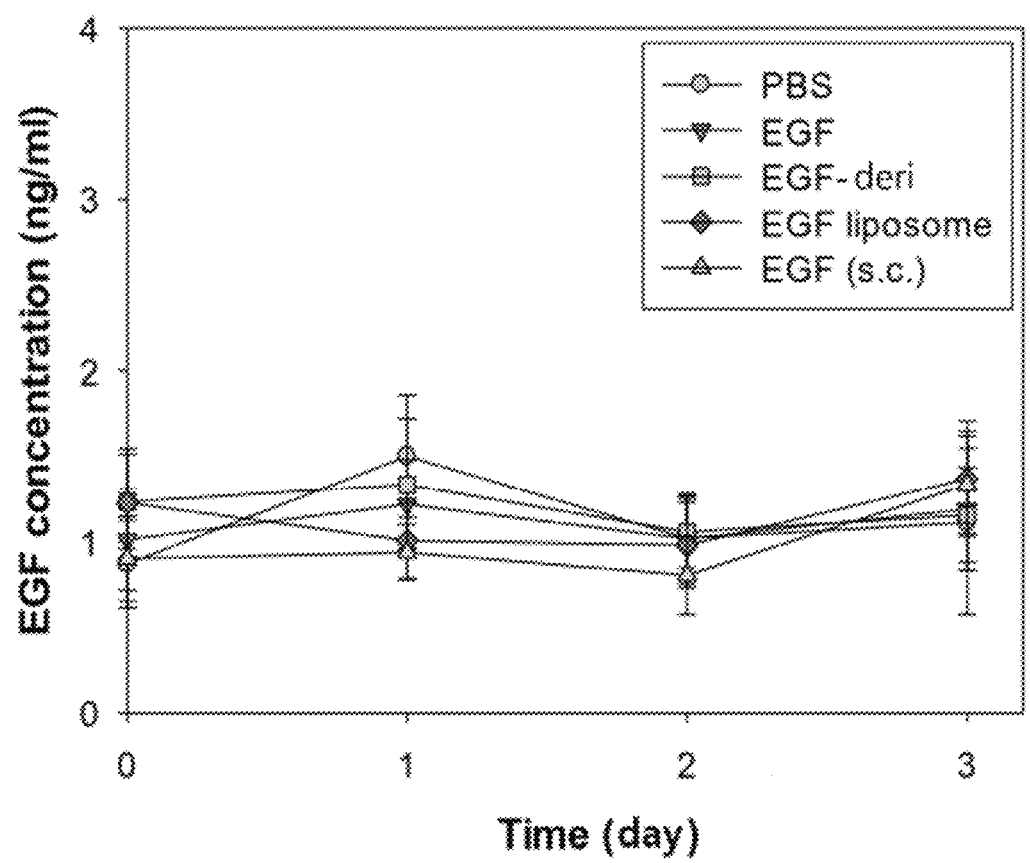

[Fig. 8A]
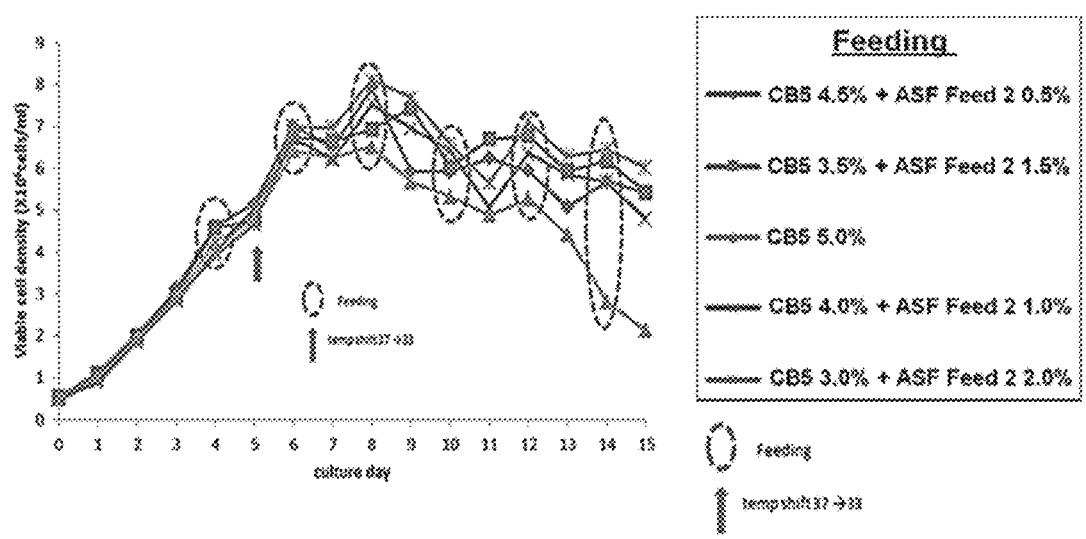

[Fig. 8B]
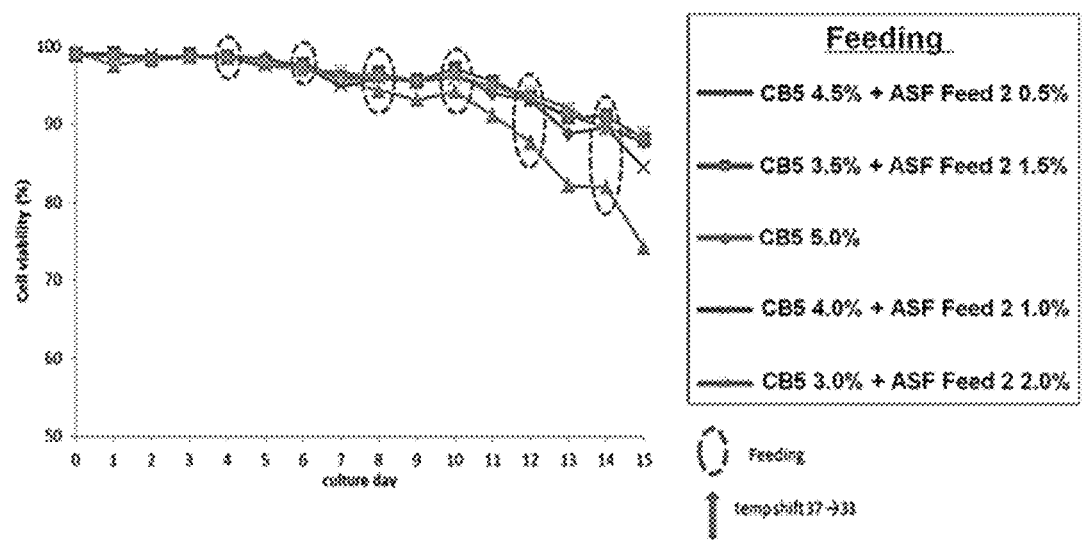

[Fig. 8C]
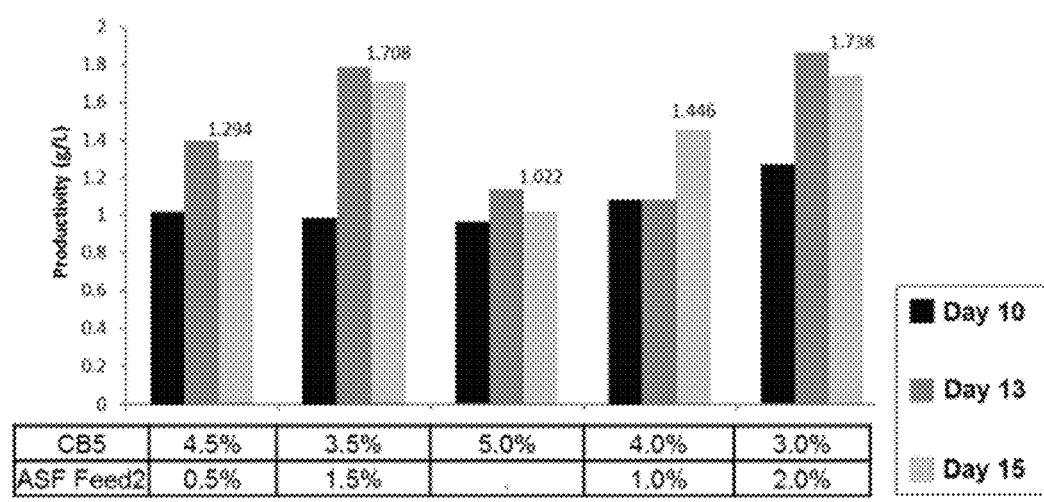

[Fig. 9A]
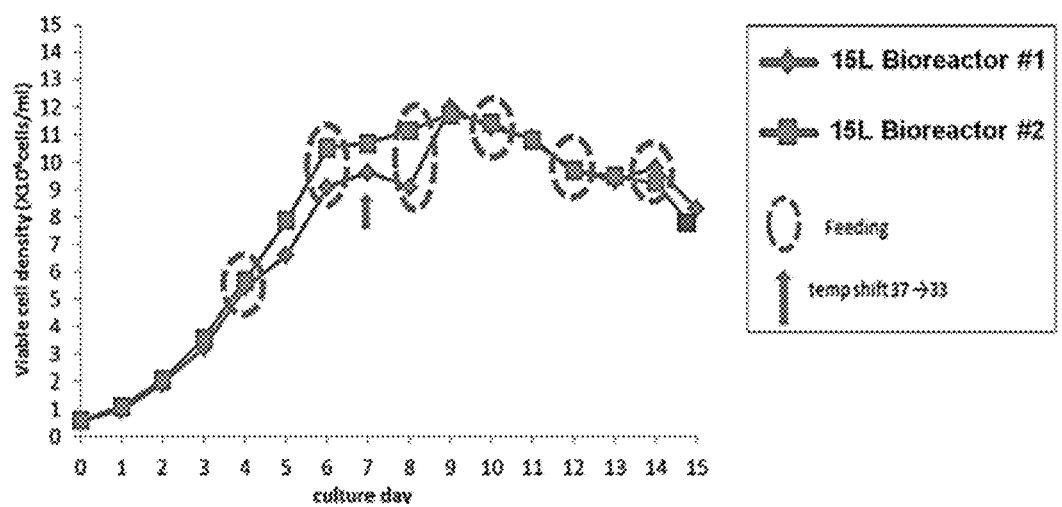

[Fig. 9B]
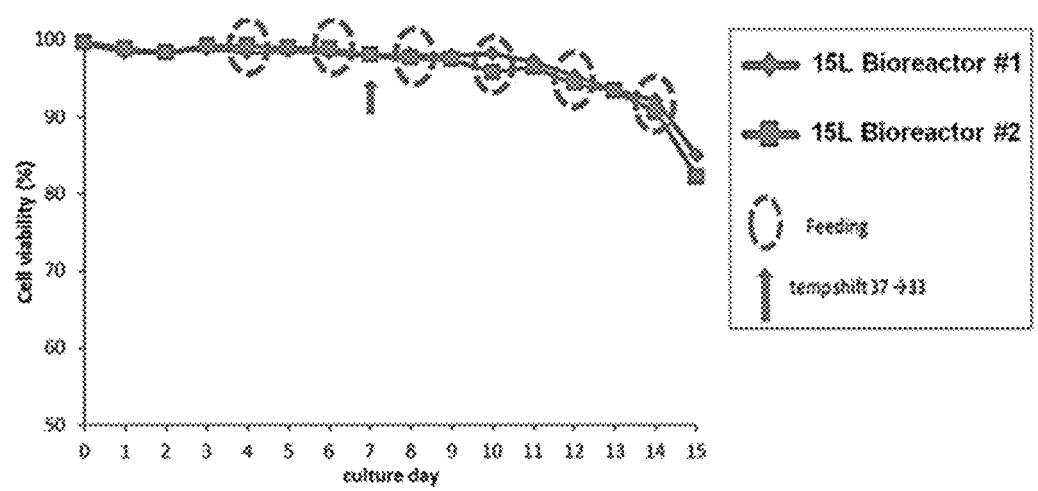

[Fig. 9C]
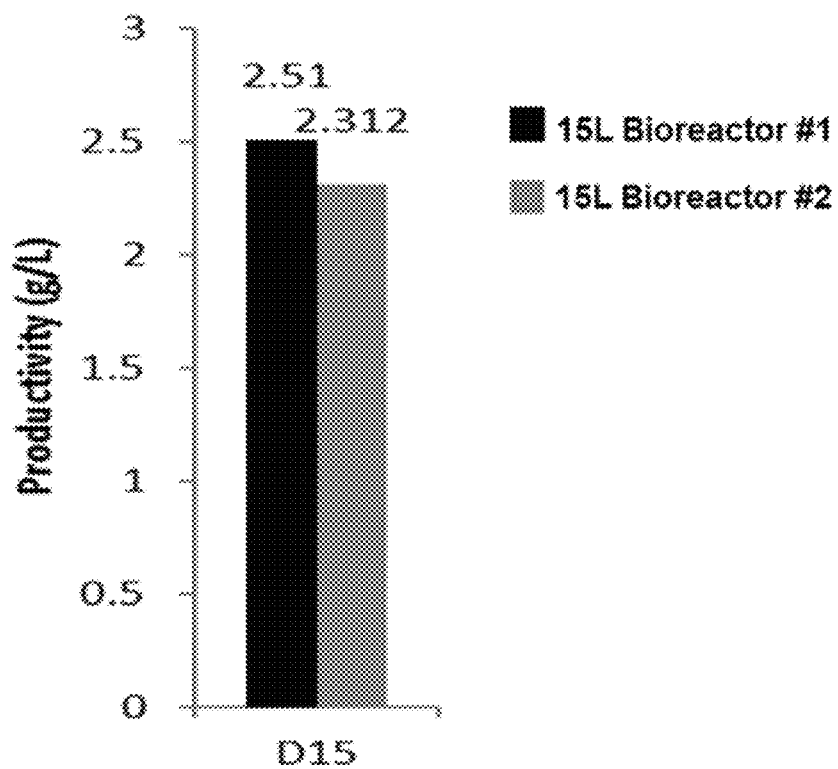

[Fig. 10A]
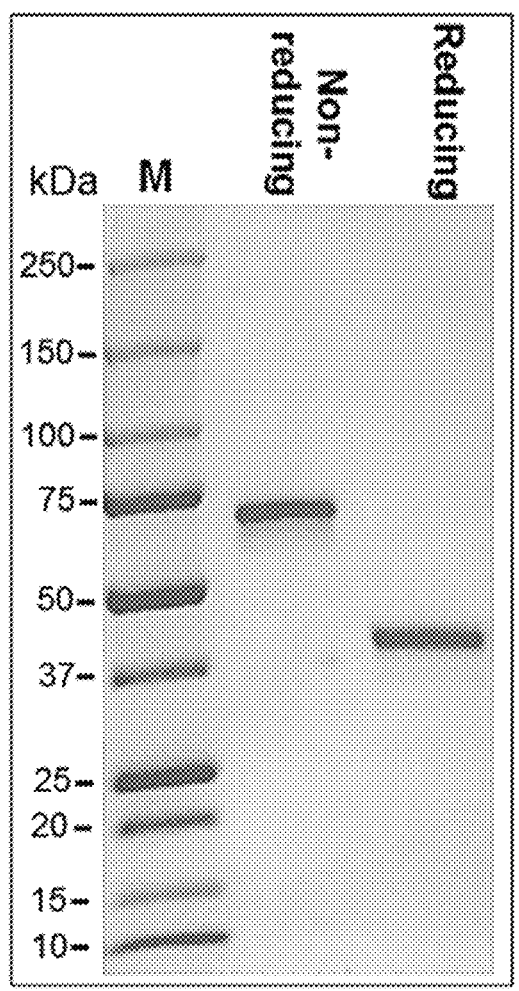

[Fig. 10B]
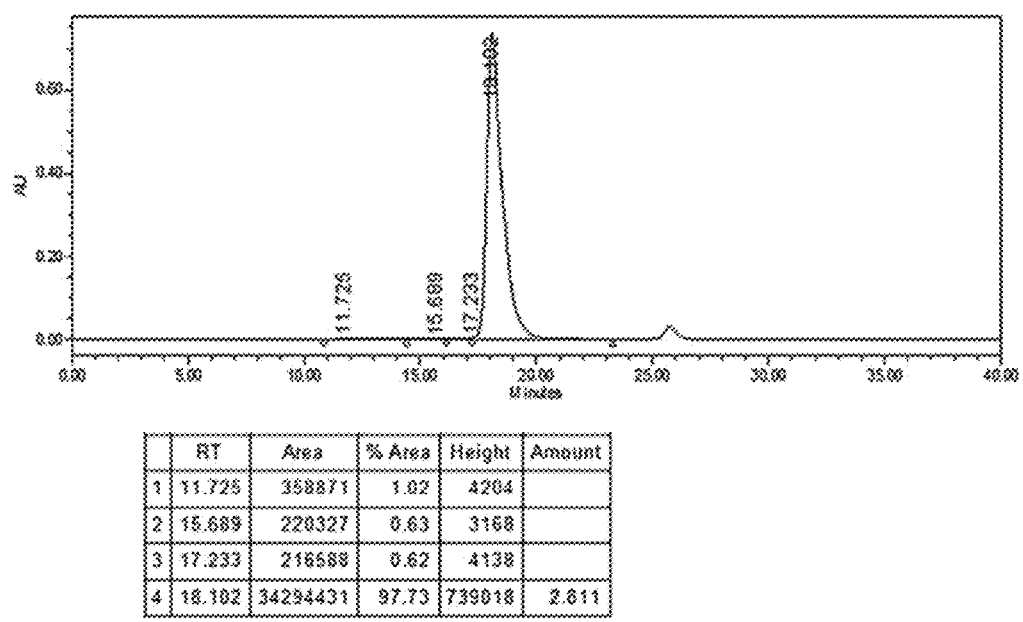

[Fig. 11]
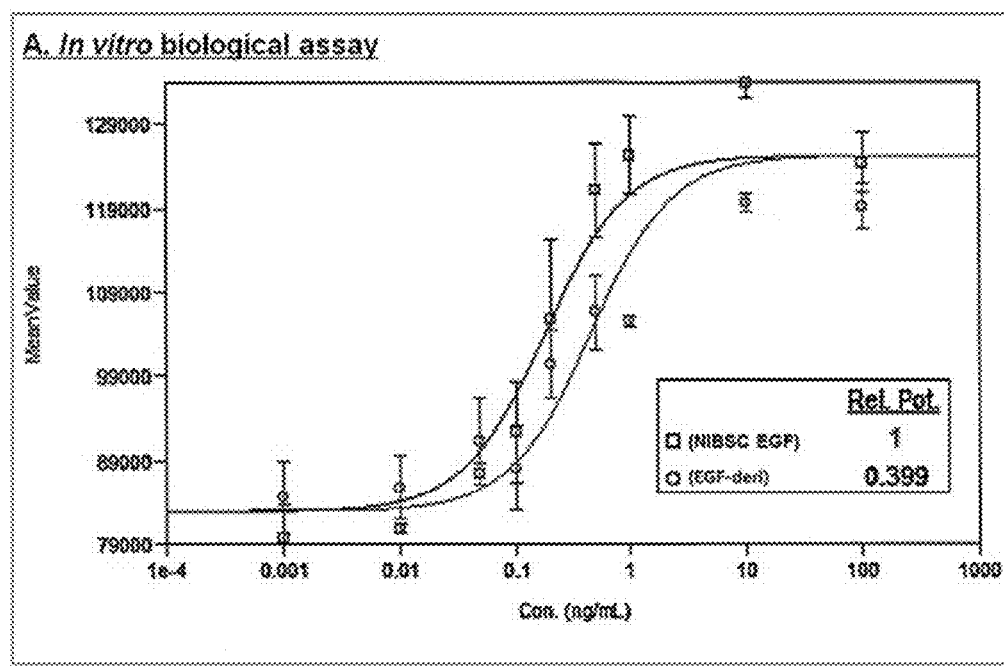

SEQUENCE LISTING

```
<160> NUMBER OF SEQ ID NOS: 5

<210> SEQ ID NO 1
<211> LENGTH: 53
<212> TYPE: PRT
<213> ORGANISM: Artificial Sequence
<220> FEATURE:
<223> OTHER INFORMATION: EGF(epidermal growth factor) amino acid
      sequence

<400> SEQUENCE: 1

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 2
<211> LENGTH: 323
<212> TYPE: PRT
<213> ORGANISM: Artificial Sequence
<220> FEATURE:
<223> OTHER INFORMATION: EGF-derivative amino acid sequence

<400> SEQUENCE: 2

Met Asp Ala Met Leu Arg Gly Leu Cys Cys Val Leu Leu Leu Cys Gly
1               5                   10                  15

Ala Val Phe Val Ser Pro Ser His Ala Asn Ser Asp Ser Glu Cys Pro
            20                  25                  30

Leu Ser His Asp Gly Tyr Cys Leu His Asp Gly Val Cys Met Tyr Ile
        35                  40                  45
```

```
Glu Ala Leu Asp Lys Tyr Ala Cys Asn Cys Val Val Gly Tyr Ile Gly
        50                  55                  60

Glu Arg Cys Gln Tyr Arg Asp Leu Lys Trp Trp Glu Leu Arg Arg Asn
 65                  70                  75                  80

Thr Gly Arg Gly Gly Glu Glu Lys Lys Gly Ser Lys Glu Lys Glu Glu
                    85                  90                  95

Gln Glu Glu Arg Glu Thr Lys Thr Pro Glu Cys Pro Ser His Thr Gln
                100                 105                 110

Pro Leu Gly Val Phe Leu Phe Pro Pro Lys Pro Lys Asp Thr Leu Met
            115                 120                 125

Ile Ser Arg Thr Pro Glu Val Thr Cys Val Val Asp Val Ser Gln
130                 135                 140

Glu Asp Pro Glu Val Gln Phe Asn Trp Tyr Val Asp Gly Val Glu Val
145                 150                 155                 160

His Asn Ala Lys Thr Lys Pro Arg Glu Glu Gln Phe Asn Ser Thr Tyr
                165                 170                 175

Arg Val Val Ser Val Leu Thr Val Leu His Gln Asp Trp Leu Asn Gly
                180                 185                 190

Lys Glu Tyr Lys Cys Lys Val Ser Asn Lys Gly Leu Pro Ser Ser Ile
                195                 200                 205

Glu Lys Thr Ile Ser Lys Ala Lys Gly Gln Pro Arg Glu Pro Gln Val
                210                 215                 220

Tyr Thr Leu Pro Pro Ser Gln Glu Glu Met Thr Lys Asn Gln Val Ser
225                 230                 235                 240

Leu Thr Cys Leu Val Lys Gly Phe Tyr Pro Ser Asp Ile Ala Val Glu
                245                 250                 255

Trp Glu Ser Asn Gly Gln Pro Glu Asn Asn Tyr Lys Thr Thr Pro Pro
                260                 265                 270

Val Leu Asp Ser Asp Gly Ser Phe Phe Leu Tyr Ser Arg Leu Thr Val
                275                 280                 285

Asp Lys Ser Arg Trp Gln Glu Gly Asn Val Phe Ser Cys Ser Val Met
                290                 295                 300

His Glu Ala Leu His Asn His Tyr Thr Gln Lys Ser Leu Ser Leu Ser
305                 310                 315                 320

Leu Gly Lys

<210> SEQ ID NO 3
<211> LENGTH: 969
<212> TYPE: DNA
<213> ORGANISM: Artificial Sequence
<220> FEATURE:
<223> OTHER INFORMATION: EGF-derivative nucleic acid sequence

<400> SEQUENCE: 3
atggacgcca tgctgagagg cctgtgctgc gtgctgctgc tgtgcggagc cgtgttcgtg      60
agccccagcc acgccaacag cgacagcgag tgcccctga gccacgatgg ctactgcctg     120
cacgatggcg tgtgcatgta catcgaggcc ctggacaagt acgcctgcaa ctgcgtggtg     180
ggctacatcg gcgagaggtg ccagtacaga gacctgaagt ggtgggagct gagaaggaac     240
accggcagag aggcgagga agaaaaggc agcaaggaga ggaggagca ggaagagaga      300 gagaccaaga cacccgagtg ccccagccac acccagcccc tgggcgtgtt cctgttccct     360
cccaagccca agacacccct gatgatcagc agaacacccg aggtgacctg cgtggtcgtg     420
gatgtgagcc aggaagatcc cgaagtgcag ttcaactggt acgtggatgg cgtggaagtg     480
```

-continued

```
cacaacgcca agaccaagcc cagagaagag cagttcaact ccacctacag agtggtgagc    540
gtgctgaccg tgctgcacca ggactggctg aacggcaagg agtacaagtg caaggtgtcc    600
aacaaaggcc tgcccagctc catcgagaag accatcagca agccaaagg ccagcccaga     660 gaacccagg tgtacaccct gcctcccagc caggaagaga tgaccaagaa ccaggtgtcc     720
ctgacctgcc tggtgaaagg cttctacccc agcgacatcg ccgtggagtg ggaaagcaac    780
ggccagcccg agaacaatta caagacaacc cctcccgtgc tggatagcga tggcagcttc    840
tttctgtaca gcagactgac cgtggacaag agcagatggc aggaaggcaa cgtgttcagc    900
tgcagcgtga tgcacgaagc cctgcacaac cactacaccc agaagagcct gtccctgagc    960
ctgggcaag                                                            969
```

<210> SEQ ID NO 4
<211> LENGTH: 298
<212> TYPE: PRT
<213> ORGANISM: Artificial Sequence
<220> FEATURE:
<223> OTHER INFORMATION: EGF-derivative amino acid sequence

<400> SEQUENCE: 4

```
Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg Arg Asn Thr Gly Arg Gly Gly Glu Glu Lys Lys
    50                  55                  60

Gly Ser Lys Glu Lys Glu Glu Gln Glu Glu Arg Glu Thr Lys Thr Pro
65                  70                  75                  80

Glu Cys Pro Ser His Thr Gln Pro Leu Gly Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser Gln Glu Asp Pro Glu Val Gln Phe Asn Trp
        115                 120                 125

Tyr Val Asp Gly Val Glu Val His Asn Ala Lys Thr Lys Pro Arg Glu
    130                 135                 140

Glu Gln Phe Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Gly Leu Pro Ser Ser Ile Glu Lys Thr Ile Ser Lys Ala Lys Gly
            180                 185                 190

Gln Pro Arg Glu Pro Gln Val Tyr Thr Leu Pro Pro Ser Gln Glu Glu
        195                 200                 205

Met Thr Lys Asn Gln Val Ser Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Arg Leu Thr Val Asp Lys Ser Arg Trp Gln Glu Gly Asn
            260                 265                 270
```

```
Val Phe Ser Cys Ser Val Met His Glu Ala Leu His Asn His Tyr Thr
            275                 280                 285

Gln Lys Ser Leu Ser Leu Ser Leu Gly Lys
    290                 295

<210> SEQ ID NO 5
<211> LENGTH: 894
<212> TYPE: DNA
<213> ORGANISM: Artificial Sequence
<220> FEATURE:
<223> OTHER INFORMATION: EGF-derivative nucleic acid sequence

<400> SEQUENCE: 5
aacagcgaca gcgagtgccc cctgagccac gatggctact gcctgcacga tggcgtgtgc        60
atgtacatcg aggccctgga caagtacgcc tgcaactgcg tggtgggcta catcggcgag       120
aggtgccagt acagagacct gaagtggtgg gagctgagaa ggaacaccgg cagaggaggc       180
gaggagaaga aaggcagcaa ggagaaggag gagcaggaag agagagagac caagacaccc       240
gagtgcccca gccacaccca gcccctgggc gtgttcctgt tccctcccaa gcccaaagac       300
accctgatga tcagcagaac acccgaggtg acctgcgtgg tcgtggatgt gagccaggaa       360
gatcccgaag tgcagttcaa ctggtacgtg gatggcgtgg aagtgcacaa cgccaagacc       420
aagcccagag aagagcagtt caactccacc tacagagtgg tgagcgtgct gaccgtgctg       480
caccaggact ggctgaacgg caaggagtac aagtgcaagg tgtccaacaa aggcctgccc       540
agctccatcg agaagaccat cagcaaagcc aaaggccagc cagagaaccc ccaggtgtac       600
accctgcctc ccagccagga agagatgacc aagaaccagg tgtccctgac ctgcctggtg       660
aaaggcttct accccagcga catcgccgtg gagtgggaaa gcaacggcca gcccgagaac       720
aattacaaga caccccctcc cgtgctggat agcgatggca gcttctttct gtacagcaga       780
ctgaccgtgg acaagagcag atggcaggaa ggcaacgtgt tcagctgcag cgtgatgcac       840
gaagccctgc acaaccacta cacccagaag agcctgtccc tgagcctggg caag            894
```

MODIFIED EGF PROTEIN, PRODUCTION METHOD THEREFOR, AND USE THEREOF

CROSS REFERENCE TO RELATED APPLICATIONS

This application is a National Stage of International Application No. PCT/KR2018/012569 filed Oct. 23, 2018, claiming priority based on Korean Patent Application No. 10-2017-0137132 filed Oct. 23, 2017; Korean Patent Application No. 10-2017-0137140 filed Oct. 23, 2017, and Korean Patent Application No. 10-2018-0125012 filed Oct. 19, 2018.

TECHNICAL FIELD

The present invention relates to a modified EGF protein, a production method therefor, and a use thereof.

BACKGROUND ART

With continuous development of the cosmetics industry, highly functional cosmetics, which are obtained by applying new technology to materials, are being developed throughout the cosmetics industry. In addition, with an increasing number is of customers who demand effects such as whitening, wrinkle improvement, and skin regeneration, functional cosmetics are becoming more valuable in the cosmetics industry, and studies for integrating various materials into cosmetics are actively being conducted. Recently, epidermal growth factor (EGF) has attracted much attention due to its excellent skin regeneration capacity and the like.

EGF is a small protein of 6 kDa and is involved in the skin regeneration process by acting on the cell nucleus to promote the division and proliferation rate of epidermal cells. In addition, this protein regulates secretion of collagen synthase and exhibits a great effect on the recovery of corneal ulcer or damage (Young Seok Kim, 2006). The EGF is widely used in cosmetics for improving skin condition, therapeutic agents for diabetic foot ulcer, wound healing agents, and the like; however, such a protein has a problem in that delivery to the wound area, persistence, and the like are relatively low. Therefore, there is a need to develop a new substance which is an EGF protein with increased in vivo permeability and persistence.

DISCLOSURE OF INVENTION

Technical Problem

The present inventors have discovered a modified EGF protein having excellent cell permeability, in vivo persistence, and stability as compared with existing EGF proteins, and thus have completed the present invention.

An object of the present invention is to provide a modified EGF protein, a production method therefor, and a use thereof.

Solution to Problem

In order to achieve the above object, the present invention provides a modified EGF protein having the amino acid sequence of SEQ ID NO: 4.

In addition, the present invention provides an expression vector comprising a polynucleotide that encodes the modified EGF protein.

In addition, the present invention provides a host cell transfected with the expression vector.

In addition, the present invention provides a method for producing a modified EGF protein, comprising the steps of:
1) culturing a host cell which produces the modified EGF protein at a temperature condition of 35° C. to 38° C.; and
2) culturing the host cell in a state where the culture temperature is lowered to a temperature of 32° C. to 34° C.

In addition, the present invention provides a cosmetic composition for improving skin condition, comprising, as an active ingredient, the modified EGF protein of the present invention.

In addition, the present invention provides a pharmaceutical composition for preventing or treating a skin disease, comprising, as an active ingredient, the modified EGF protein of the present invention.

Advantageous Effects of Invention

The modified EGF protein according to the present invention binds to the cell membrane so that EGF can be effectively delivered into the cell, thereby exhibiting increased cell permeability and half-life. In addition, the modified EGF protein has enhanced long-term stability in that EGF is kept in an intact form under severe conditions. Thus, this protein can be very effectively applied to cosmetic compositions and pharmaceutical compositions, which have a short shelf life and are difficult to store and distribute, due to protein denaturation. In addition, a method for producing a modified EGF protein according to the present invention allows the modified EGF protein to be produced in an active form, and can be used commercially because such a method may be carried out with an excellent productivity through establishment of optimal culture temperature and pH conditions. In an embodiment of the present invention, a modified EGF protein is produced with a productivity of 2.3 g/L or higher and a purification yield of 75% or higher, demonstrating superiority of is the method for producing a modified EGF protein according to the present invention. Therefore, the modified EGF protein of the present invention is superior to existing EGF proteins in terms of cell permeability, and persistence and stability in vivo, and thus can be used as a cosmetic composition or a pharmaceutical composition.

BRIEF DESCRIPTION OF DRAWINGS

FIGS. 4A to 4C graphically illustrate activity of the EGF-deri protein over time under a severe condition. Here, FIG. 4A illustrates activity of the EGF-deri protein at an initial stage; FIG. 4B illustrates activity of the EGF-deri protein after 2 months; and FIG. 4C illustrates activity of the EGF-deri protein after 3 months.

FIG. 5 graphically illustrates changes in activity of the EGF-deri protein over time depending on the number of freezing and thawing (F/T) repetitions. Here, the F/T cycle was repeated a total of 5 times.

FIG. 6 illustrates results obtained by subjecting the skin of Balb/c mice and SKH-1 hairless mice to treatment with each of FITC-labeled PBS, EGF, EGF-deri, and EGF liposome proteins, and after 6 hours and 12 hours, analyzing permeability of each protein for respective skin layers through confocal fluorescence microscopy.

FIG. 7 illustrates results obtained by subjecting the skin of Balb/c mice and SKH-1 hairless mice to treatment with each of FITC-labeled PBS, EGF, EGF-deri, and EGF liposome proteins, and then measuring the EGF concentration in blood over time. Here, EGF (s.c.) means a group injected subcutaneously with EGF.

FIGS. 8A to 8C illustrate results used to select the optimal combination condition of supplements in developing a culture process.

FIGS. 9A to 9C illustrate viable cell density, viability, and productivity under the final established culture condition.

FIGS. 10A and 10B illustrate purification yield and purity obtained according to the established purification process.

FIG. 11 illustrates in vitro activity of EGF-deri protein relative to standard EGF.

BEST MODE FOR CARRYING OUT THE INVENTION

Figure 1:
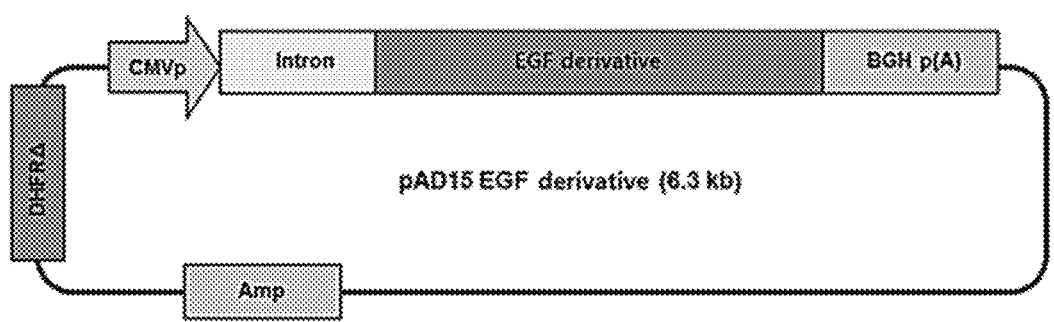
FIG. 1 illustrates a schematic diagram of the structure of a gene construct capable of expressing EGF-deri protein.

In an aspect of the present invention, there is provided a modified EGF protein having the amino acid sequence of SEQ ID NO: 2 or SEQ ID NO: 4.

As used herein, the term "EGF" refers to a protein (SEQ ID NO: 1) having a molecular weight of 6 kDa and consisting of 53 amino acids. The EGF promotes the division and proliferation rate of epidermal cells, thereby acting to recover skin damage, promote healing of corneal ulcer, regenerate the skin, or the like, and functioning to form new blood vessels, proliferate fibroblasts, secrete collagen synthase, or the like.

As used herein, the term "modified EGF protein" may refer to EGF-derivative (hereinafter referred to as EGF-deri). In the present invention, the EGF-deri may have the amino acid sequence of SEQ ID NO: 4, which may be encoded by the nucleotide sequence of SEQ ID NO: 5. In addition, in an embodiment, the EGF-deri may contain a signal sequence. The EGF-deri containing the signal sequence may have the amino acid sequence of SEQ ID NO: 2, which may be encoded by the nucleotide sequence of SEQ ID NO: 3. In an embodiment of the present invention, the EGF-deri not only has increased in vivo delivery and persistence relative to standard EGF, but also may retain protein activity for a long period of time even under severe conditions. Thus, the EGF-deri can be very effectively applied to cosmetic compositions, which have a short shelf life and are difficult to store and distribute, due to protein denaturation.

In another aspect of the present invention, there are provided an expression vector comprising a polynucleotide that encodes the modified EGF protein, and a host cell transfected with the expression vector. Here, the expression vector may be pAD15 EGF derivative. In addition, the host cell may be a Chinese hamster ovary cell (CHO cell). In an embodiment of the present invention, the expression vector pAD15 EGF derivative expressing EGF-deri protein was constructed using an expression vector system (ProGen, Korea). Subsequently, the vector was transfected into Chinese hamster ovary (CHO)-DG44 DHFR(−) cells, and then a screening process was performed twice to select a cell line in which the EGF-deri protein is expressed at a high level.

In yet another aspect of the present invention, there is provided a method for producing a modified EGF protein, comprising the steps of: 1) culturing a host cell which produces the modified EGF protein at a temperature condition of 35° C. to 38° C.; and 2) culturing the host cell in a state where the culture temperature is lowered to a temperature of 32° C. to 34° C. Here, the host cell may be a Chinese hamster ovary cell, and the modified EGF protein may have the amino acid sequence of SEQ ID NO: 2 or SEQ ID NO: 4.

In the method for producing a modified EGF protein of the present invention, the culture in step 1) and/or step 2) may be fed-batch culture. As used herein, the term "fed-batch culture" refers to a culture method in which nutrient medium is gradually added to a culture vessel at the same time as culture begins, and a culture solution is not withdrawn from the culture vessel until the end of culture. In the fed-batch culture, the concentration of a specific substance in culture may be controlled to a predetermined set value by causing a rate of addition of the substance to be proportional to a rate of consumption thereof by microorganisms.

As used herein, the term "medium (or media)" refers to a nutrient solution for maintenance, growth, proliferation, or expansion of cells in an artificial in vino environment outside of a multicellular organism or tissue. The medium may be optimized for culturing particular cells, and examples thereof include basal culture medium prepared for supporting cell growth, production medium prepared for promoting production of monoclonal antibodies, and concentrated medium prepared by concentrating nutrients to a high concentration. The basal culture medium refers to a medium capable of supporting minimal cell growth. The basal culture medium supplies standard inorganic salts such as zinc, iron, magnesium, calcium, and potassium, as well as trace elements, vitamins, energy sources, buffer systems, and amino acids. The basal culture medium according to the present invention may be used during the early stage of culture which is a cell growth phase. In an embodiment of the present invention, Hycell CHO medium was used as the basal culture medium.

The method for producing a modified EGF protein according to the present invention includes a step of culturing a host cell, which produces the modified EGF protein of the present invention, at 35° C. to 38° C. Specifically, the culture may be performed at a temperature of 37° C. and at a pH condition of 6.8 to 7.3.

The step of culturing the host cell at 35° C. to 38° C. is a step for growing the cell, during which rapid cell growth occurs. In general, a culture condition for cell growth may vary depending on the type of cell, the type of target protein to be produced, and the like. For the CHO cell used in the present invention, it is known that the number of cells is most actively increased at a temperature of 37° C. and at a pH range of 6.8 to 7.3.

Meanwhile, in the culture phases of the present invention, the cell growth phase may be 3 to 8 days, specifically 4 to 7 days, from the beginning of culture. According to an embodiment of the invention, the cell growth phase may be 7 days from the beginning of culture. In addition, according to an embodiment of the present invention, a culture temperature during the cell growth phase may be 37'C.

The method for producing a modified EGF protein according to the present invention includes a step of culturing the host cell in a state where the culture temperature is lowered to 32° C. to 34° C. Here, the culture temperature may be lowered when the number of cells cultured in step 1)

reaches 6×10⁶ to 9×10⁶ cells/mi. Specifically, the culture may be performed at a temperature of 33'C and at a pH condition of 6.8 to 7.1.

When the culture temperature for the cell is lowered according to the above step, the cell enters a protein production phase under a culture condition for maximizing target protein is production. For entry from the cell growth phase to the protein production phase, the culture condition may be changed when the viable cell density caused by culture reaches about 80% to 90% of the maximum viable cell density. According to an embodiment of the present invention, the culture condition may be changed when the viable cell density reaches about 90/o.

Here, according to an embodiment of the present invention, the culture temperature for the cell at which entry from the cell growth phase to the protein production phase takes place may be 33° C. If the culture temperature is 35° C. or higher, there is a problem that the produced modified EGF protein becomes unstable; and if the culture temperature is 31° C. or lower, there is a problem that decreased productivity is exhibited because the cells do not grow to a sufficient number. In addition, change of the culture temperature according to the present invention may be performed at day 6 to day 8 of culture; and according to an embodiment of the present invention, such change may be performed at day 7 of culture. On the other hand, in the method for producing a modified EGF protein of the present invention, the period of time, during which the culture is performed in a state where the culture temperature is lowered to 32° C. to 34° C., is 7 to 12 days, specifically 8 to 10 days, from the end of the culture performed at 35° C. to 38° C.

The term "viable cell density (VCD)" refers to the amount or number of living cells in a given area. In the present invention, in order to produce a target protein with high efficiency, viable cell density is measured to change the culture condition when an appropriate number of cells are viable. The viable cell density may be determined by measuring the absorbance of cells.

In addition, in the present invention, in the step of culturing the host cell, a supplement may be supplied to the basal culture medium for protein production. As used herein, the term "supplement" refers to a substance additionally contained in basal culture medium for sufficiently supplying nutrients so that a cell can produce a protein while maintaining its health when the cell enters a protein production phase. In general, the supplement includes lipids, amino acids, vitamins, growth factors, and the like. Types of supplements that can be used for protein production are well known in the art, and examples thereof include, but are not limited to, ActiCHO (GE Healthcare), Cell Boost (GE Healthcare), ASF Feed2 (Ajinomoto Co., Inc.). Specifically, the supplement may be Cell Boost (CB)5 and ASF Feed2.

The supplements may be added in an appropriate amount for a high level of recombinant protein production, and these may be used individually or in combination. The supplement may be added starting from a time point which is immediately before the cell passes through the growth phase and enters the protein production phase. According to the culture of the present invention, the supplement may be added starting from 1 to 3 days before the temperature is lowered for protein production. According to an embodiment of the present invention, the supplement may be added starting from 3 days before the temperature is lowered for protein production. The supplement should be continuously added from the viewpoint that such a supplement is consumed during cell survival and protein production. In general, the supplement may be added periodically at intervals of 1 to 3 days from the addition date thereof. In an embodiment of the present invention, the supplement was added at intervals of 2 days.

When CB5 is used as a supplement, the concentration of CB5 may be 3.0% to 5.0%. In an embodiment, the concentration of CB5 may be, but is not limited to, 3.0%, 3.5%, 4.0%, 4.5%, or 5.0%, with 3.0% being preferred. In addition, when ASF Feed2 is used as a supplement, the concentration of ASF Feed2 may be 0.5% to 2%. In an embodiment, the concentration of ASF Feed2 may be, but is not limited to, 0.5%, 1%, 1.5%, or 2%, with 2.0% being preferred. In addition, in the step of culturing the host cell, CB5 or ASF Feed2 as a supplement may be applied individually or in combination.

In an embodiment of the present invention, in order to find the optimal combination condition of supplements for producing a modified EGF protein, CB5 or ASF Feed2 as a supplement was applied during culture under the following combinations: CB5 4.5%+ASF Feed2 0.5%, CB5 3.5%+ASF Feed2 1.5%, CB5 5.0%, CB5 4.0%+ASF Feed21.0%, or CB5 3.0%+ASF Feed2 2.0%. As a result, when CB5 or Feed2 is added as a supplement during culture, excellent viable cell density, cell viability, and modified EGF protein productivity were observed; and in particular, the best result was observed for the combination of CB5 3.0%+ASF Feed2 2.0%.

The culture for producing a modified EGF protein according to the present invention may last for 10 to 20 days, specifically 12 to 18 days, and according to an embodiment of the present invention, the culture may last for 15 days.

In addition, the method for producing a modified EGF protein according to the present invention may further include a step of purifying the modified EGF protein obtained from a culture solution. Affinity chromatography may be performed to purify and obtain the modified protein with high yield. In particular, it is possible to obtain the modified EGF protein by affinity chromatography using a column filled with Protein A-coupled resin, that is, using Protein A as a ligand of resin.

As used herein, the term "culture solution" refers to a culture medium after culture of a cell, which contains various factors including a protein produced and secreted by the cell, and may be obtained by removing the cell by centrifugation after completion of the culture.

The term "affinity chromatography" refers to one of chromatography methods in which one of two types of substances having highly specific biological affinity to each other is used as a stationary phase and separation of a target substance is achieved using difference in affinity for the stationary phase. Therefore, in the step of obtaining a modified EGF protein from the culture solution, the culture solution may be purified by a column filled with Protein A-coupled resin.

The resin used for the affinity chromatography is composed of a matrix, a hydrophilic crosslinking agent, and a ligand. Here, the matrix may be cross-linked agarose, for example, highly cross-linked high-flow agarose. The ligand may be Protein A that is a protein specifically binding to the modified EGF protein of the present invention. In the resin, a modified EGF protein is covalently linked to an agarose fragment, and thus may selectively bind to the modified EGF protein. In addition, since the ligand in the resin has a long hydrophilic crosslinking agent, the target protein to be separated may be easily bound thereto. An example of the resin may be MabSelect.

As used herein, the term "Protein A" refers to a protein capable of recognizing, as an epitope, a specific subunit of the modified EGF protein having the amino acid sequence of SEQ ID NO: 2 or 4, and specifically binding thereto. According to an embodiment of the present invention, in a column filled with Protein A-coupled resin, the modified EGF protein may be eluted with a glycine solution. The solution may be used at an appropriate concentration and pH, which may prevent the target protein from binding to Protein A, to the extent that such a solution does not alter the quality and activity of the target protein. An appropriate concentration range for the solution may be 50 mM to 150 mM; and according to an embodiment of the present invention, the solution may have a concentration of 0.1 M. On the other hand, an appropriate pH range for the solution may be 3.4 to 4.4; and according to an embodiment of the present invention, the solution may have a pH of 3.8.

In an embodiment of the present invention, when a purification process is performed by the above established method, high protein yield and purity are observed, as compared with commonly known EGF production, while showing similar activity.

Therefore, in a method for producing a modified EGF protein according to the present invention, not only a simple and economical production process is used, but also the produced modified EGF protein has excellent activity, which allows the modified EGF protein produced by the above method to be supplied to consumers at a lower price.

In addition, in still yet another aspect of the present invention, there is provided a cosmetic composition for improving skin condition, comprising, as an active ingredient, the modified EGF protein produced according to the method for producing a modified EGF protein of the present invention.

Here, the improving skin condition means protecting the skin from deterioration or loss of function of skin cells or improving skin condition, selected from the group consisting of inhibition of wrinkle formation, inhibition of skin aging, improvement in skin elasticity, skin regeneration, injury or wound healing, corneal regeneration, alleviation of skin irritation, and combinations thereof.

In the present invention, there is provided a method for improving skin condition, using the cosmetic composition. The method for improving skin condition may include a step of applying, to the skin of a subject in need thereof, a cosmetic composition according to the present invention. The subject may be a mammal, specifically a human.

The step for applying, to the skin, a cosmetic composition according to the present invention may include directly applying or spraying the cosmetic composition to the skin, depending on its formulation. Here, application amount and number of daily uses of the cosmetic composition may be appropriately set depending on the user's age, sex, intended use, severity of symptoms, and the like. For example, an appropriate amount of the cosmetic composition may be applied to the skin at a frequency of 1 to 6 times per day.

In addition, in still yet another aspect of the present invention, there is provided a pharmaceutical composition for preventing or treating a skin disease, comprising, as an active ingredient, the modified EGF protein produced according to the method for producing a modified EGF protein of the present invention.

Here, the skin disease may be selected from the group consisting of foot ulcer, pressure ulcer, oral mucositis, burn, and combinations thereof.

The pharmaceutical composition may further comprise a pharmaceutically acceptable carrier. The carrier may be contained in an amount of about 1% to about 99.99% by weight, 5% to 90% by weight, 10% to 85% by weight, 20% to 60% by weight, and preferably about 90% to about 99.99% by weight, based on the total weight of the pharmaceutical composition of the present invention.

In the present invention, there is provided a method for preventing or treating a skin disease, using the pharmaceutical composition.

The method for preventing or treating a skin disease may include a step of applying, to the skin of a subject in need thereof, the pharmaceutical composition according to the present invention. The subject to which the pharmaceutical composition can be applied may be a mammal, specifically a human.

The step of applying, to the skin, the pharmaceutical composition according to the present invention may include directly applying or spraying the pharmaceutical composition to the skin, depending on its formulation. Here, application amount and number of daily uses of the pharmaceutical composition may be appropriately set depending on the user's age, sex, intended use, severity of symptoms, and the like. For example, an appropriate amount of the pharmaceutical composition may be applied to the skin at a frequency of 1 to 6 times per day.

MODE FOR THE INVENTION

Hereinafter, the present invention will be described in more detail by way of the following examples. However, the following examples are only for illustrating the present invention, and the scope of the present invention is not limited thereto.

Example 1. Construction of Expression Vector for Modified EGF Protein and Development of Cell Line Expression vector pAD15 EGF-derivative expressing EGF-deri protein was constructed using an expression vector system (ProGen, Korea). Here, the structure of a gene construct inserted into the expression vector is shown in FIG. 1. The vector was transfected into Chinese hamster ovary (CHO)-DG44 DHFR(−) cells, and then high expression monoclonal cell lines were screened twice. Dihydrofolate reductase (DHFR) is an enzyme essential for the synthesis of deoxythymidine monophosphate (dTMP), one of the four components required for gene replication which is a cell proliferation process. The substance HT (hypoxanthine and thymidine) is a precursor to dTMP and can be used by cells to synthesize dTMP.

Before CHO-DG44 DHFR(−) cells were transfected with an expression vector containing DHFR gene, culture must be performed in medium containing HT in order to allow for cell growth. Therefore, after transfection with the expression vector, culture was performed in medium not containing HT so that only cell lines, into which a plasmid expressing the target gene and DHFR had been stably inserted to expresses the DHFR protein, survived and were selected. This is called a HT selection step. After selecting the cell lines expressing DHFR and EGF-deri proteins through the HT selection step, high expression cell lines were selected is while increasing the concentration of methotrexate (MTX), a potent inhibitor of DHFR enzyme, in a stepwise manner. Then, cell lines having a productivity of 60 μg/$10^6$ cells/day to 80 μg/$10^4$ cells/day at a MTX concentration of 1 μM were selected. Then, cell lines having a productivity of 60 μg/$10^6$ cells/day to 80 μg/10 cells/day at a MTX concentration of 1 μM were selected. The selected six cell lines, as shown in Table 1 below, were selected as RCB candidate cell lines.

TABLE 1

| | Monoclonal cell line | Productivity | |
|---|---|---|---|
| | | (μg/ml) | (μg/10$^6$ cells) |
| MTX | A | 115 | 63 |
| (1 μM) | B | 123 | 69 |
| | C | 100 | 64 |
| | D | 103 | 60 |
| | E | 109 | 67 |
| | F | 109 | 68 |

Example 2. Identification of Expression of EGF-Deri Protein

In order to identify whether EGF-deri protein was well expressed in the selected six RCB candidate cell lines, SDS-PAGE was performed on culture solutions of the six cell lines. Here, the culture solutions loaded on respective lanes are shown in Table 2, and the SDS-PAGE results for the respective culture solutions are shown in FIG. 2.

TABLE 2

| Lane # | Sample |
|---|---|
| 1 | Standard Marker |
| 2 | CHO-DG44 DHFR(−) culture solution |
| 3 | CHO-DG44 DHFR(−) A |
| 4 | culture solution in B |
| 5 | which EGF-deri protein C |
| 6 | is stably expressed D |
| 7 | E |
| 8 | F |

Figure 2:
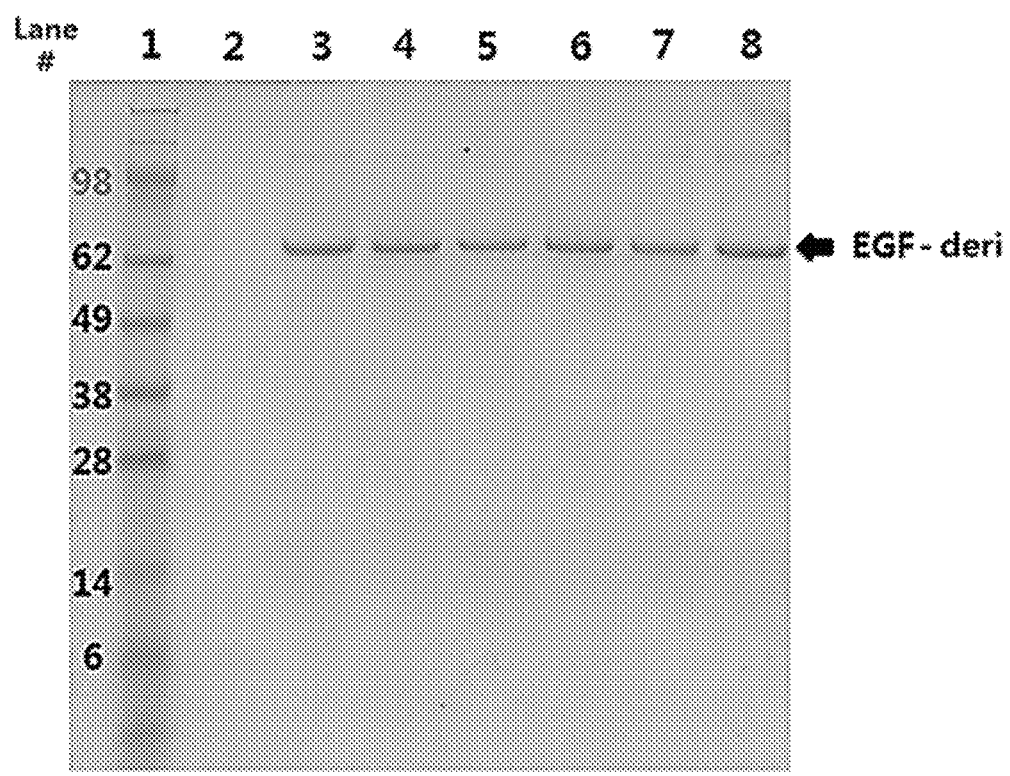
FIG. 2 illustrates results obtained by performing SDS-PAGE on the EGF-deri protein that has been expressed in each of selected six research cell bank (RCB) candidate cell lines.

As shown in FIG. 2, it was identified that the EGF-deri protein has a molecular weight of about 62 kDa. In addition, in the culture solutions of the selected six cell lines, the EGF-deri protein accounted for 80% or higher thereof. For the EGF-deri proteins, most of them were present in an active monomeric form (62 kDa), 5% or lower of them were also observed in a dimeric form (124 kDa), and no cleaved form was observed.

Experimental Example 1. Identification of Long-Term Passage Stability of RCB Candidate Cell Lines In order for a certain cell line to be used as a cell line for pharmaceutical product production, productivity and doubling time should be kept constant within a set criterion during the time period until the production is completed. When each of the RCB cell lines selected in Example 1 was made, via a master cell bank (MCB), into a working cell bank (WCB), about 10 or more passages were required. In addition, when main culture of 200 L or higher was intended, 5 or more passages were required for seed culture, and 20 or more passages were required for the main culture. Therefore, in order for the RCB cell line to be used for pharmaceutical product production, productivity and doubling time should be kept stable during 35 or more passages. In order to identify this, productivity and doubling time of the EGF-deri protein were measured for each of the selected RCB candidate cell lines. For productivity measurement, a cell culture in culture was first centrifuged and suspended to a concentration of $5 \times 10^1$ cells/ml as a new culture solution. Subsequently, 5 ml of the suspension was cultured in a T-25 flask for 3 days. Then, 1 ml of the culture solution was taken, of which 0.5 ml was used to measure the cell number; and the remaining 0.5 ml was centrifuged and the supernatant was used to measure, with human IgG ELISA, productivity per $1 \times 10^6$ cells. The doubling time (Td) was measured as follows. The cell solution in culture was inoculated at $0.3 \times 10^6$ cells/ml in a 125 ml flask and incubated for 3 days. Then, the cell number was measured. Calculation was performed using the following expression: Td=ln 2/m (m=ln x2−ln x1/t2−t1). t1 and t2 are the start and end times of incubation, and x1 and x2 are the viable cell numbers before and after incubation. Among the selected RCB candidate cell lines, a cell line showing the best long-term passage stability was selected as the final cell line for pharmaceutical product development. For cell line F selected as the final cell line, the productivity and doubling time measured during 35 passages are shown in Table 3 below and FIG. 3.

TABLE 3

| Passages | Productivity (μg/ml) | Percentage (%) |
|---|---|---|
| P1-7 | 49.41 | 100 |
| P8-14 | 52.64 | 106.54 |
| P15-21 | 55.75 | 112.84 |
| P22-28 | 65.10 | 131.76 |
| P29-35 | 57.57 | 116.5 |

Figure 3:
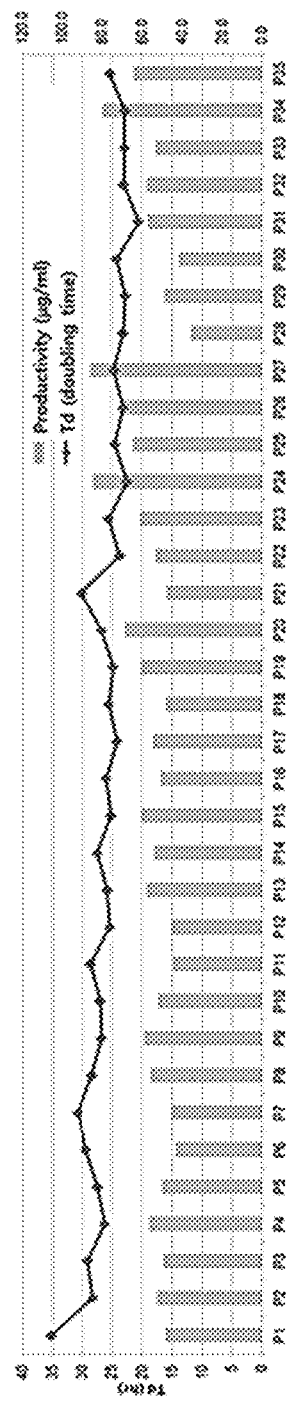
FIG. 3 graphically illustrates productivity and doubling time of the EGF-deri protein measured during 35 passages, in order to identify long-term passage stability of the final cell line.

As shown in Table 3 and FIG. 3, for the final cell line, the productivity was kept in a range of 100% to 132%, and the doubling time was kept constant at around 25 hours. This indicates that the selected final cell line can be used as a cell line for pharmaceutical product production.

Experimental Example 2. Identification of Stability of EGF-Deri Protein Under Severe Condition In order to identify stability of the EGF-deri protein under a severe condition, 126 μg/ml of EGF-deri protein was stored for 3 months under a severe condition of a temperature of 40° C. and a relative humidity of 75±5%, and activity of the substance EGF-deri was observed. An amount of the EGF-deri protein over time is shown in Table 4 below, and activity of the EGF-deri protein over time is shown in Table 5 below and FIGS. 4A to 4C.

TABLE 4

| | Initial | Month 1 | Month 2 | Month 3 |
|---|---|---|---|---|
| EGF-deri protein | 100% (12 ± 3 μg/ml) | 79% (99 ± 9 μg/ml) | 49.5% (62 ± 6 μg/ml) | 32.0% (41 ± 3 μg/ml) |

TABLE 5

| | Criterion | Initial | Month 2 | Month 3 |
|---|---|---|---|---|
| EGF-deri protein | ED$_{50}$ vaule indicated | 0.2 ± 0.04 ng/ml | 0.22 ± 0.05 ng/ml | 0.19 ± 0.04 ng/ml |

As shown in Table 4, morphology of the EGF-deri protein gradually decreased to 79%, 49.5%, and 32% over time under a severe condition of 40° C. However, as shown in Table 5 and FIGS. 4A to 4C, biological activity of the EGF-deri protein was mostly retained. This indicates that although partial degradation of the EGF-deri protein occurred under a severe condition, most of the degraded EGF-deri substances were normal EGF's and retained activity. From these results, it was found that the EGF-deri protein exhibited high stability from the viewpoint of retaining activity with little loss even under a severe condition.

Experimental Example 3. Formulation of EGF-Deri Protein, and Freezing and Thawing Thereof 50 mM Tris-HCl with a pH of 7.2±0.2 was used as a formulation buffer for the EGF-deri protein. Then, the EGF-deri protein formulated with the buffer was stored frozen at a temperature of −80° C. to −70° C. Freezing and thawing (F/T) cycle of the formulated EGF-deri protein was repeated a total of 5 times. The results are shown in Table 6 below and FIG. 5.

TABLE 6

| Sample | Peak 1 | Peak 2 | Main Peak | Increment of Peak 2 for each cycle |
|---|---|---|---|---|
| EGF-deri protein (control) | 0.06 | 0.17 | 99.77 | |
| EGF-deri protein (1 F/T) | 0.07 | 0.92 | 99.01 | 0.75 |
| EGF-deri protein (2 F/T) | 0.06 | 1.4 | 98.54 | 0.48 |
| EGF-deri protein (3 F/T) | 0.07 | 1.76 | 98.17 | 0.36 |
| EGF-deri protein (4 F/T) | 0.05 | 2.18 | 97.76 | 0.42 |
| EGF-deri protein (5 F/T) | 0.06 | 2.46 | 97.48 | 0.28 |

As shown in Table 6 and FIG. 5, as the number of freezing and thawing cycles for the EGF-deri protein increased, Peak 2 increased and Main Peak decreased. During the first freezing and thawing cycle, Peak 2 showed the highest increase, and when the freezing and thawing cycle was repeated a total of 5 times, Main Peak decreased by about 2%. In conclusion, the EGF-deri protein maintained a purity of about 97% or higher even after a total of 5 freezing and thawing cycles. From these results, it was found that the EGF-deri protein exhibited high stability from the viewpoint of retaining activity with little loss even under a severe condition in which a freezing and thawing cycle was repeated.

Experimental Example 4. Analysis of Skin Permeation of EGF-Deri Protein

In order to examine skin permeability of the EGF-deri protein, hair-removed Balb/c mice and SKH-1 hairless mice were prepared as experimental animals. Using two types of mice, that is, Balb/c mice of which hair had been removed from the back skin using epilation cream, and genetically hairless mice, it was examined whether skin permeability of the EGF-deri protein differs depending on artificial damage of the skin caused by hair removal. The two types of mice were divided into PBS group, EGF group, EGF-deri group, and EGF liposome (H&A PharmaChem) group, respectively, depending on the protein to be applied on the skin. Here, each protein was labeled with fluorescein isothiocyanate (FITC), a fluorescent labeling reagent, so that skin permeability of the individual protein could be identified. A solution of each protein labeled with FITC was dropped, in an amount of 200 ng based on FITC, on the skin of each group of mice, and applied using a brush.

Experimental Example 4.1. Transdermal Delivery of EGF-Deri Protein

When 6 hours and 12 hours had passed after the solution of each protein labeled with FITC was applied on the back skin of each group of mice, the mice were sacrificed and skin tissues were removed therefrom. The skin tissues were stored in their longitudinal section using a cryostat, and then permeability thereof for respective skin layers was analyzed through a confocal fluorescence microscope. The results are shown in FIG. 6.

As shown in FIG. 6, 6 hours and 12 hours after the transdermal delivery, FITC signals were observed in the hypodermis layer of the mice belonging to the EGF-deri group. This pattern was equally observed regardless of the mouse species. In addition, such skin permeability was similar to that of liposome commonly known as an efficient delivery system for transdermal delivery. In the permeability by transdermal delivery during the experiment, despite differences between individuals, the overall pattern was similar enough to be reproducible. This indicates that the EGF-deri protein had high skin permeability.

Experimental Example 4.2. Blood Collection Experiment for Evaluating Safety of EGF-Deri Protein The solution of each protein labeled with FITC was applied on the back skin of each group of mice, and then the EGF concentration in blood over time was measured through eye-bleeding. The results are shown in FIG. 7.

As shown in FIG. 7, no increase or change in EGF concentration in blood was observed in all of the EGF group, the EGF-deri group, and the EGF liposome group, as compared with the PBS group, a negative control. This was equally observed even in a group subcutaneously injected with EGF. This indicates that the amount of EGF delivered into the blood was very low relative to the EGF concentration in blood, and that EGF was rapidly enzymatically decomposed in the body and did not affect the EGF concentration in blood in the long term. In addition, it was found from these results that the EGF-deri protein can be safely used as a cosmetic or pharmaceutical product.

Experimental Example 5. Identification of Cell Culture Condition for Production of Modified EGF Protein Experimental Example 5.1. Identification of Optimal Supplement In order to establish the optimal condition of supplements for the production of modified EGF protein, cells were cultured under various combination conditions of supplements. First, clones at $0.5 \times 10^5$ cells/ml were cultured for 6 days at 37° C. in Hycell CHO medium (HyClone, USA) (growth phase); and the temperature was switched to 33° C. and then the clones were cultured until day 15 (production phase). Here, concerning the culture pH, culture was performed at pH 6.9 to 7.3 during the growth phase, and at pH 6.9 to 7.1 during the production phase. The agitation speed for culture, which had started from 150 rpm, was increased to 200 rpm at day 4 of culture and increased to 250 rpm at day 6 of culture. Glucose was kept at 3.0 g/L or higher each day.

In order to find the optimal combination condition of supplements, Cell Boost 5 (CB5, GE Healthcare, USA) and ASF Feed2 (Ajinomoto Co., Inc.) as supplements were added as the following combinations at day 4, day 6, day 8, day 10, day 12, and day 0.14 of culture: CB5 4.5%+ASP Feed2 0.5%, CB5 3.5%+ASF Feed2 1.5%, CB5 5.0%, CB5 4M % ASF Feed2 1.0%, and CB5 3.0% ASF Feed2 2.0%. This is specifically shown in Table 7 below and FIGS. 8A to 8C.

TABLE 7

| Item | | | Contents | Note |
|---|---|---|---|---|
| Culture mode | | | Fed-Batch | Fixed |
| Basal media | | | Hycell CHO | Fixed |
| Seeding density | | | $0.5 \times 10^6$ cells/mL | Fixed |
| Temperature | Growth | | 37° C. | Fixed |
| | Production | | 33° C. at day 7 of culture | Fixed |
| pH | Growth | | 6.9 to 7.3 (Set point: 7.1) | Fixed |
| | Production | | 6.9 to 7.1 (Set point: 7.0) | Fixed |
| Supplements | Test conditions | 1 | Cell Boost (CB)5 4.5% + ASF Feed2 (Ajinomoto Co., Inc.) 0.5% | Needs to be optimized |
| | | 2 | Cell Boost (CB)5 3.5% ASF Feed2 (Ajinomoto Co., Inc.) 1.5% | |
| | | 3 | Cell Boost (CB)5 5.0% | |
| | | 4 | Cell Boost (CB)5 4.0% + ASF Feed2 (Ajinomoto Co., Inc.) 1.0% | |
| | | 5 | Cell Boost (CB)5 3.0% + ASF Feed2 (Ajinomoto Co., Inc.) 2.0% | |
| Treatment days | | | Days 4, 6, 8, 10, 12, and 14 of culture | Fixed |
| Agitation speed | | | 150 rpm ⓡ 200 rpm (day 4 of culture) ⓡ 250 rpm (day 6 of culture) | Fixed |
| Glucose | | | ≥3.0 g/L | Fixed |
| Culture duration (days) | | | 15 | Fixed |

As shown in FIG. 8A, viable cell density (VCD) values ranged from $7.0 \times 10^6$ cells/mL to $8.0 \times 10^6$ cells/mL under the conditions of CB5 3.0%+ASF Feed2 2.0%, CB5 4.0%+ASF Feed2 1.0%, and CB5 3.5%+ASF Feed2 1.5%. Among these, the best VCD value was observed under the condition of CB5 3.0%+ASF Feed2 2.0%. In addition, as shown in FIG. 8B, among the five different combination conditions of supplements, the best result was observed under the conditions of CB5 3.0%+ASF Feed2 2.0% and CB5 3.5%+ASF Feed2 1.5% in that cell viability was kept at 90% or higher during the 15-day culture. In addition, as shown in FIG. 8C, at the end of the culture (at day 15), productivity of the modified EGF protein was 1.0 g/L under the condition of CB5 5.0%, 1.294 g/L under the condition of CB5 4.5%+ASF Feed2 0.5%, 1.44 g/L under the condition of CB5 4.0%+ ASF Feed2 1.0%, 1.70 g/L under the condition of CB5 3.5%+ASF Feed2 1.5%, and 1.74 g/L, which was the highest productivity, under the condition of CB5 3.0%+ASF Feed2 2.0%.

From these results, it was found that the optimal combination condition of supplements for producing the modified EGF protein was CB5 3.0%+ASF Feed2 2.0%.

Experimental Example 5.2. Identification of Viable Cell Density, Cell Viability, and Productivity of EGF Protein Under Established Optimal Condition As shown in Table 8 below, using Hycell CHO as basal media in fed-batch method, inoculation was made at a concentration of $0.5 \times 10^6$ cells/mL under the optimal combination condition of supplements for producing the modified EGF protein which had been established in Experimental Example 5.1. The culture temperature was kept at 37° C. until day 7 of culture, that is, during a growth phase, and then at 33° C. until day 15 of culture. Concerning the culture pH, culture was performed under a condition of pH 6.9 to 7.3 during the culture at 37° C. (growth phase), and performed under a condition of pH 6.9 to 7.1 during the culture at 33° C. (production phase). The agitation speed for culture, which had started from 150 rpm, was increased to 200 rpm at day 4 of culture and increased to 250 rpm at day 6 of culture. The glucose concentration was kept at 3.0 g/L or higher throughout the culture period. At days 4, 6, 8, 10, 12, and 14 of culture, a combination of CB5 3.0%+ASF Feed2 2.0% was added as a supplement. The results are shown in FIGS. 9A to 9C.

TABLE 8

| Item | | Contents | Note |
|---|---|---|---|
| Culture mode | | Fed-Batch | Fixed |
| Basal media | | Hycell CHO | Fixed |
| Seeding density | | $0.5 \times 10^6$ cell/mL | Fixed |
| Temperature | Growth | 37° C. | Fixed |
| | Production | 33° C. at day 7 of culture | Fixed |
| pH | Growth | 6.9 to 7.3 (Set point: 7.1) | Fixed |
| | Production | 6.9 to 7.1 (Set point: 7.0) | Fixed |
| Supplements | Test conditions | Cell Boost (CB)5 3.0% + ASF Feed2 (Ajinomoto Co., Inc.) 2.0% | Fixed |
| Treatment days | | Days 4, 6, 8, 10, 12, and 14 of culture | Fixed |
| Agitation speed | | 150 rpm ⓡ 200 rpm (day 4 of culture) ⓡ 250 rpm (day 6 of culture) | Fixed |
| Glucose | | ≥3.0 g/L | Fixed |
| Culture duration (days) | | 15 | Fixed |

As shown in FIGS. 9A to 9C, referring to the results obtained through two batches, the VCD values ranged from $8.0 \times 10^6$ cells/mL to $12.0 \times 10^6$ cells/mL (FIG. 9A); and the cell was 90% or higher until day 14 of culture and 80% or higher at day 15 which was the last culture day (FIG. 9B). Productivity of the modified EGF was 2.3 g/L or higher (FIG. 9C). The results are summarized in Table 9 below. From the above results, it was found that a process with far superior culture productivity relative to the standard EGF was established.

TABLE 9

| Item | Contents |
|---|---|
| Maximum cell density | ≥11 × $10^6$ cells/mL |
| Viability at day 15 of culture | ≥80% |
| Productivity | ≥2.3 g/L |

Experimental Example 5.3. Purification of Modified EGF Protein

The optimized purification method for EGF-deri is as follows. First, a column having Protein A as a stationary phase was prepared with a Mabselect system, and the prepared cell supernatant was loaded onto the column to have an amount of 14 g protein/L. Subsequently, impurities were removed by sequentially using wash buffer 1 of pH 7.0 composed of 50 mM sodium phosphate and 500 mM NaCl, and wash buffer 2 of pH 4.5 composed of 50 mM sodium acetate. Subsequently, the modified EGF protein was eluted while injecting, into the column, an elution buffer of pH 3.8 composed of 100 mM glycine. The experimental results are shown in Table 10 below, and FIGS. 10A and 10B.

TABLE 10

| Item | Contents | Note |
|---|---|---|
| Purfication yield | ≥75% | — |
| Purity | ≥97% | — |

As shown in FIGS. 10A and 10B, from the SDS-PAGE and size-exclusion HPLC (SE-HPLC) results, it was found that the modified EGF protein was well purified. In addition, as shown in Table 10, the purified modified EGF protein had a purification yield of 75% or higher and a purity of 97% or higher.

Experimental Example 6. Comparison of Biological Activity of Standard EGF and EGF-Deri In order to compare biological activity of standard EGF and EGF-deri, an experiment was conducted in the following manner. Here, the standard EGF used in this experiment was obtained from the National Institute for Biological Standards and Control (NIBSC).

First, NRK-49F cell line (ATCC CRL-1570, rat kidney) was cultured in culture medium (5% newborn calf serum (Gibco, Cat #2610-074)+DMEM (ATCC, Cat #30-2002™)+ 1% Antibiotic (Gibco, Cat #15240-062)). Subsequently, on the day of the experiment, $0.5 \times 10^3$ cells were seeded to each well of a 96-well plate in a volume of 50 mL using assay medium (0.5% newborn calf serum (Gibco, Cat #2610-074)+DMEM (ATCC, Cat #30-2002™)). Then, the two samples, NIBSC EGF and EGF-deri, were diluted with the same assay medium so that the final concentrations thereof were 100 ng/mL, 10 ng/mL, 1 ng/mL, 0.5 ng/mL, 0.2 ng/mL, 0.1 ng/mL, 0.05 ng/mL, 0.01 ng/mL, and 0.001 ng/mL, respectively, and added to each well of the plate in a volume of 50 mL. Subsequently, culture was performed for 72 hours in a 5±0.5% $CO_2$ incubator at 37±0.5° C. After completion of the culture, 100 mL of Cell titer-Glo 2.0 reagent was dispensed per well, and then reaction was allowed to proceed at room temperature for 10 minutes in a light-shielded state. Subsequently, measurement was performed under the following condition: luminescence integration of 500 and emission of Lm 1. $E_{C50}$ values were calculated based on the measurement. The results are shown in FIG. 11.

As shown in FIG. 11, EGF-deri, a modified EGF protein of the present invention, had biological activity similar to the standard EGF purchased from NIBSC.

The invention claimed is:

1. A modified EGF protein comprising the amino acid sequence of SEQ ID NO: 4.

2. The modified EGF protein of claim 1, wherein the modified EGF protein comprising the amino acid sequence of SEQ ID NO: 4 is encoded by the nucleotide sequence of SEQ ID NO: 5.

3. An expression vector comprising a polynucleotide encoding the modified EGF protein of claim 1.

4. A cell line transfected with the expression vector of claim 3.

5. The cell line of claim 4, wherein the cell line is a Chinese hamster ovary cell (CHO cell).

6. A method for producing the modified EGF protein of claim 1, comprising the steps of:
   1) culturing a host cell line which comprises a nucleic acid encoding the modified EGF protein at a temperature of 35° C. to 38° C.; and
   2) culturing the host cell line under conditions for expression of the modified EGF protein at a temperature of 32° C. to 34° C.

7. The method of claim 6, wherein the culture in step 1) is performed for 3 to 8 days.

8. The method of claim 6, wherein the culture temperature in step 1) is about 37° C.

9. The method of claim 6, wherein the culture in step 1) is performed at a pH condition of 6.8 to 7.3.

10. The method of claim 6, wherein the culture in step 2) is performed for 7 to 12 days.

11. The method of claim 6, wherein the culture temperature in step 2) is about 33° C.

12. The method of claim 6, wherein the culture in step 2) is performed at a pH condition of 6.8 to 7.1.

13. The method of claim 6, wherein the step 1) is performed until the number of cells reaches $6 \times 10^6$ to $9 \times 10^6$ cells/ml, and the step 2) is performed with the temperature adjusted to 32° C. to 34° C.

14. The method of claim 6, wherein the culture in step 1) and or step 2) is fed-batch culture.

15. The method of claim 6, further comprising purifying the modified EGF protein obtained from a culture solution.

16. The method of claim 15, wherein the purification is carried out by affinity chromatography.

17. The method of claim 16, wherein a Protein A-coupled resin is used in the affinity chromatography.

18. The method of claim 6, wherein the host cell line is a Chinese hamster ovary cell (CHO cell).

19. A composition comprising as an active ingredient the modified EGF protein of claim 1.

20. The composition of claim 19, which is a cosmetic composition.

21. The composition of claim 19, which is a pharmaceutical composition and further comprises a pharmaceutically acceptable carrier.

22. A method of improving skin condition and/or treating skin disease, comprising administering to a subject in need thereof an effective amount of the composition of claim 19.

23. The method of claim 22, comprising applying the composition to a target site of skin of the subject.

24. The method of claim 23, wherein the improving skin condition is selected from the group consisting of inhibition of wrinkle formation, inhibition of skin aging, improvement in skin elasticity, skin regeneration, injury or wound healing, corneal regeneration, alleviation of skin irritation, and a combination thereof.

25. The method of claim 22, wherein the skin disease is selected from the group consisting of foot ulcer, pressure ulcer, oral mucositis, burn, and a combination thereof.

* * * * *